United States Patent [19]
Walsh

[11] Patent Number: 6,019,222
[45] Date of Patent: Feb. 1, 2000

[54] APPARATUS AND KIT FOR EXAMINING A SPECIMEN

[76] Inventor: Valentine Walsh, 3 Whitehorse Mews, London SE1 7QD, United Kingdom

[21] Appl. No.: 08/938,425

[22] Filed: Sep. 26, 1997

[30] Foreign Application Priority Data

Sep. 27, 1996 [GB] United Kingdom ................... 9620205

[51] Int. Cl.⁷ .................................................. B65D 85/48
[52] U.S. Cl. .......................................... 206/456; 206/569
[58] Field of Search .................................... 206/569, 570, 206/572, 575, 456

[56] References Cited

U.S. PATENT DOCUMENTS

| | | | |
|---|---|---|---|
| 2,633,980 | 4/1953 | Jorgensen | 206/456 |
| 4,440,301 | 4/1984 | Intengan | 206/456 |
| 4,763,791 | 8/1988 | Halverson et al. | 206/570 |
| 4,819,804 | 4/1989 | Levy | 206/456 |
| 4,979,515 | 12/1990 | Briggs et al. | 206/569 |
| 5,449,071 | 9/1995 | Levy | 206/569 |
| 5,515,974 | 5/1996 | Higson | 206/570 |
| 5,611,433 | 3/1997 | Levy | 206/569 |
| 5,624,638 | 4/1997 | Negrotti | 206/569 |

*Primary Examiner*—David T. Fidei
*Attorney, Agent, or Firm*—Flynn, Thiel, Boutell & Tanis, P.C.

[57] ABSTRACT

The invention relates to apparatus for examining a flake of a painting, wall, ceiling or the like, comprising a body and receptacle in the body for receiving the flake, the receptacle having a flat base, and the body including a receptacle for an identification which is offset from the well. The body is transparent, is polished and is cuttable to expose an internal surface of the flake for examination. Thus the characteristics of the flake can be assessed, which is useful in restoration work. The invention may be put up in a kit.

16 Claims, 1 Drawing Sheet

1

APPARATUS AND KIT FOR EXAMINING A SPECIMEN

FIELD OF THE INVENTION

The invention relates to a mould, particularly to a mould which comprises apparatus for examining a specimen.

BACKGROUND OF THE INVENTION

Specimens such as flakes of paint are often examined by art historians or restorers in order to try to disclose the kind of paint used by the artist. This is often necessary when an "old master" is being restored. It is essential to know the kind of paint used, and varnish so that when the whole picture is subject to restoration, the correct techniques can be used in order that the correct action and materials are utilised so that the cleaning or restoration process does not adversely effect, or even destroy the picture being restored. This is often the case in buildings too, where the original paint is examined to try to restore the building as near as possible to the original. In both cases, a flake of the paint applied to the canvas or wall is usually taken, and is then examined under say a microscope.

The flake is usually several layers of paint and varnish and is usually positioned on a microscope slide or other carrier and is "fixed" with a layer of resin. The whole surface of the carrier then needs to be polished, and the carrier is cut through and the specimen is at the same, time cut through to be examined on the cut surface. However, the specimen is often not mounted squarely, and a clear view cannot be obtained.

It is among the objects of this invention to seek to mitigate these disadvantages.

According to one aspect of the invention there is apparatus for examining a specimen, comprising a body, and a receptacle in the body for a specimen to be examined, the arrangement being such that the specimen can be fixed in the receptacle for examination.

The receptacle may comprise a blind bore in the body. This is a relatively simple yet efficient construction, particularly as the blind bore may have a substantially planar base for ease of accuracy of viewing of a specimen.

There may be means to identify the specimen comprising a recess in the body. This provides a way of avoiding mixing of specimens.

The recess may be elongate, and its axis may be parallel to and offset from a diameter of the bore.

The body may comprise a transparent material, particularly a material which may be cuttable.

The body may be polished.

According to as second aspect of the invention there may be provided a kit for examining a specimen, comprising a magnifying device, apparatus as hereinbefore defined, and means for holding a specimen in the receptacle.

The magnifying device may comprise a microscope.

The means for holding a specimen may comprise curable transparent resin, which may be in a tube.

The kit may include means to cut through the body to expose a surface of the specimen for examination in use.

The cutting means may comprise a saw.

The kit may be mounted in a case, which may be portable.

The case may have a respective compartment at least for the magnifying device, apparatus, and means for holding the specimen.

The compartments may each have a configuration similar to the respective item received therein for ease of storage and transport.

BRIEF DESCRIPTION OF THE DRAWINGS

Apparatus embodying the invention is hereinafter described, by way of example, with reference to the accompanying drawings.

DETAILED DESCRIPTION

Figure 3:
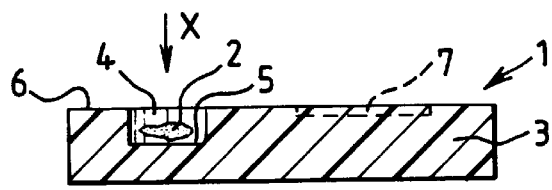
FIG. 3 is a sectional view on line 3—3 of FIG. 2 with a specimen in position for examination.

Referring to the drawings, there is shown apparatus 1 for examining a specimen, for example a flake 2 (FIG. 3) of a painting, comprising a body 3, and a receptacle 4 in the body 3 for a specimen 2 to be examined, the arrangement being such that the specimen 2 can be fixed in the receptacle 4 for examination. Thus the receptacle 4 is in the embodiment a blind well having a flat bottom 5 and which is cylindrical, the well 4 being formed in a surface 6 of the material of the body by machining, for example by drilling, though it could be moulded in the body 3 or by any other suitable means. The body 3 is formed from a transparent material such as plexiglass or perspex and is rectangular in shape and is portable, cuttable, and is polished on all its flat surfaces so as to permit good light transmission. The size in the embodiment is 30 mm×10 mm×5 mm. The well 4 is of 5 mm diameter and has a depth of 3 mm, though it will be understood that these dimensions are not critical. The well 4 thus is let into the major surface 6 of the body 3 in which there is means 7 for identifying a specimen 2 in the form of an elongate recess or depression, the longitudinal axis of which is offset from a diameter of the well 4 and is substantially parallel thereto.

There may be a groove, line or other indicia (not shown) in or on the surface of the body 3 to indicate an optimum line of cut, as described below.

Figure 1:
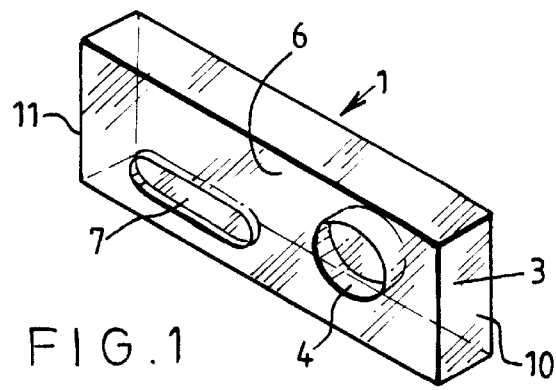
FIG. 1 is a perspective view of apparatus for examining a specimen.
Figure 2:
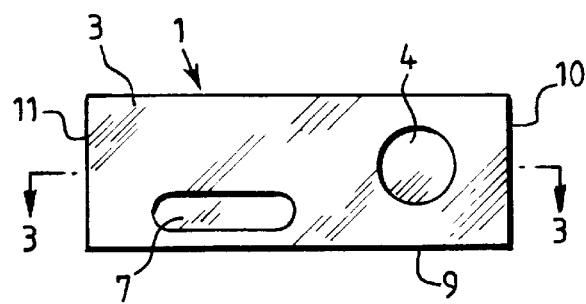
FIG. 2 is a plan view of the apparatus of FIG. 1.

In use to examine a painting, wall, ceiling etc. being researched and/or restored, a flake 2 of paint is taken therefrom of a size to fit into the well 4 and to lie as flat as possible on the bottom 5 of the well. The specimen 2 is then secured in position by pouring a resin into the well 4 and allowing it to cure, the resin being transparent. An identification tag, label or indicia is inserted in the recess 7 and secured thereto as by glue or further resin, so that the surface 6 of the body remains flat, there being no resin proud thereof in the receptacle or the well. When the resin is cured, the body 3 is sliced by cutting or sawing along the line 3—3, FIG. 2, and thus through the flake 2, preferably centrally thereof to expose a clean or internal edge or surface of the flake 2 of paint. The flake of paint is then examined by viewing it through a viewing device such as a magnifying glass, eye-piece or microscope 8 (FIG. 4) in the direction of the arrow 'X', FIG. 3, the body 3 standing for this purpose on the side 9 opposite the cut surface.

The flake 2 is then examined.

It will be understood that by slicing along the line 3—3 the identification means 7 is not destroyed or disrupted, so the flake 2 being examined is always identifiable, this lack of disruption being provided for by the offsetting of the recess 7 from the line 3—3 of cut, through being substantially parallel thereto. Moreover, as the boundary surfaces of the body 3 are flat, as is the base 5 of the well, when the body mounted on say a slide or table for examination under a microscope an observer can view the cut edge of the specimen squarely, which assists in assessment of the characteristics of the flake.

Stated in another way, the specimen is fixed securely in a precise position relative to the microscope for accurate viewing, and assessment for analysis. The nature of the original paint can then be identified, which is particularly useful in study and/or research into older paintings, and for restoration work.

It will be understood too that the apparatus 1 may be modified. Thus there may be more than one well 4, each with its own offset identifying recess 7 and moreover there may be a well or wells in an end face 10 or 11 of the body 3.

Figure 4:
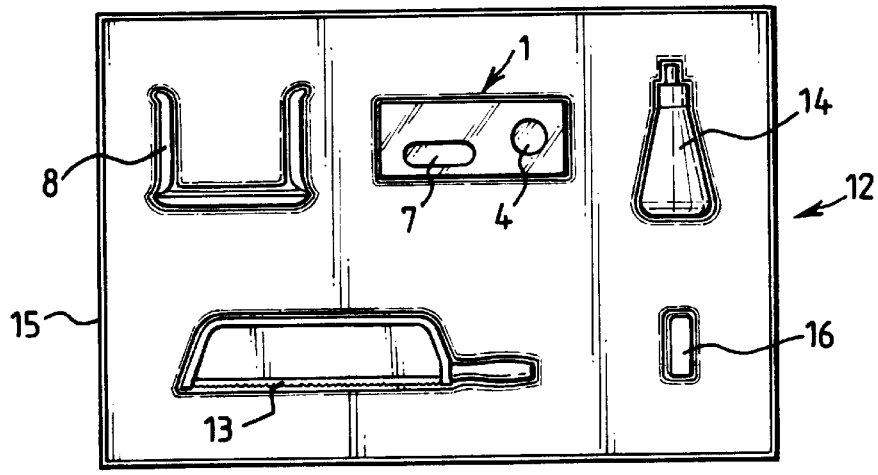
FIG. 4 is a schematic plan view of a kit, for examining a specimen, according to the invention.

In every embodiment, the apparatus 1 may form part of a kit 12, as shown in FIG. 4, which is one possible kit embodying the invention and which comprises the apparatus 1, a viewing device in the form of a microscope 8, which may be hand held or portable, a device 13 in the form of a small hand saw for slicing or sawing the body, and a tube 14 of resin or glue for securing the flake 2 and an identifying tag or label in the body 3. The kit 12 may be housed in a box 15 which may have respective compartments which may have a configuration which corresponds with the shape of a particular item of the kit.

The box may be portable, and may include an instructions box or leaflet, and a supply of plain identification tags or labels 16 in a recess or receptacle.

I claim:

1. Apparatus for examining a specimen, comprising
   (i) a body;
   (ii) a receptacle in the body for a specimen to be examined, whereby the specimen is fixed in the receptacle for examination; and
   (iii) means to identify the specimen comprising a recess in the body.

2. Apparatus as defined in claim 1, wherein the receptacle comprises a blind bore in the body.

3. Apparatus as defined in claim 2, wherein the blind bore has a substantially planar base.

4. Apparatus as defined in claim 1, wherein the recess is elongate.

5. Apparatus as defined in claim 2, wherein the longitudinal axis of the recess is offset from and substantially parallel to a diameter of the bore.

6. Apparatus as defined in claim 1, wherein the body is a transparent material.

7. Apparatus as defined in claim 1, wherein the body is cuttable.

8. Apparatus as defined in claim 1, wherein the body is polished.

9. A kit for examining a specimen, comprising
   (i) a magnifying device;
   (ii) a body;
   (iii) a receptacle in the body for a specimen to be examined, whereby the specimen is fixed in the receptacle for examination; and
   (iv) means for holding a specimen in the receptacle.

10. A kit as defined in claim 9, wherein the magnifying device comprises a microscope.

11. A kit as defined in claim 10, wherein the means for holding a specimen comprises curable transparent resin.

12. A kit as defined in claim 10, wherein the kit includes means to cut through the body to expose a surface of the specimen for examination in use.

13. A kit as defined in claim 12, wherein the cutting means comprises a saw.

14. A kit as defined in claim 10, wherein said kit is mounted in a case.

15. A kit as defined in claim 14, wherein the case has a respective compartment at least for the magnifying device, body, and means for holding the specimen.

16. A kit as defined in claim 15, wherein the case has a respective compartment at least for the magnifying device, body, and means for holding the specimen and wherein said compartments each have a configuration similar to the respective item received therein.

* * * * *

UNITED STATES PATENT AND TRADEMARK OFFICE
CERTIFICATE OF CORRECTION

PATENT NO. : 6,019,222
DATED : February 1, 2000
INVENTOR(S) : Valentine Walsh

Page 1 of 1

It is certified that error appears in the above-identified patent and that said Letters Patent is hereby corrected as shown below:

Title Page:
Under [30] Foreign Application Priority Data
change "9620205" to -- 9620205.6 --.

Column 4:
Line 24, change "claim 10" to -- claim 9 --.
Line 26, change "claim 10" to -- claim 9 --.
Line 31, change "claim 10" to -- claim 9 --.
Line 36, change "claim 15" to -- claim 14 --.

Signed and Sealed this

Twenty-first Day of August, 2001

*Attest:*

NICHOLAS P. GODICI
*Attesting Officer*   Acting Director of the United States Patent and Trademark Office